United States Patent
Orellana Moraleda et al.

(10) Patent No.: US 8,986,436 B2
(45) Date of Patent: Mar. 24, 2015

(54) LUMINESCENT PIGMENTS AND THEIR USE IN SECURITY APPLICATIONS

(75) Inventors: Guillermo Orellana Moraleda, Madrid (ES); David García Fresnadillo, Madrid (ES); Paloma Varela García De Oteyza, Madrid (ES); Javier Gamo Aranda, Madrid (ES); José Miguel Silván Pobes, Madrid (ES); Fernando Álvarez Martínez, Madrid (ES); Andrés Ruiz Quevedo, Madrid (ES)

(73) Assignee: Fábrica Nacional de Moneda y Timbre—Real Casa de la Moneda, Madrid (ES)

( * ) Notice: Subject to any disclaimer, the term of this patent is extended or adjusted under 35 U.S.C. 154(b) by 0 days.

(21) Appl. No.: 13/984,710

(22) PCT Filed: Feb. 10, 2012

(86) PCT No.: PCT/EP2012/052307
§ 371 (c)(1),
(2), (4) Date: Oct. 18, 2013

(87) PCT Pub. No.: WO2012/107558
PCT Pub. Date: Aug. 16, 2012

(65) Prior Publication Data
US 2014/0158019 A1    Jun. 12, 2014

(30) Foreign Application Priority Data
Feb. 11, 2011   (EP) ..................................... 11382034

(51) Int. Cl.
C09D 11/00   (2014.01)
C09K 11/06   (2006.01)
C07F 15/00   (2006.01)
B42D 15/00   (2006.01)

(52) U.S. Cl.
CPC ............ *C07F 15/0053* (2013.01); *B42D 15/00* (2013.01); *C09K 11/06* (2013.01); *C09D 11/00* (2013.01); *C09K 2211/185* (2013.01)
USPC ................ 106/31.77; 106/31.78; 252/301.16; 252/301.25; 252/301.26; 252/301.27; 252/301.28; 252/301.29; 252/301.31; 252/301.32

(58) Field of Classification Search
CPC ... C09D 11/00; C09K 11/06; C09K 2211/185
USPC ............................ 106/31.77, 31.78, 493, 498; 252/301.16, 301.25, 301.26, 301.27, 252/301.28, 301.29, 301.31, 301.32
See application file for complete search history.

(56) References Cited

U.S. PATENT DOCUMENTS

| | | | | |
|---|---|---|---|---|
| 5,324,457 A * | 6/1994 | Zhang et al. | ............. | 252/301.33 |
| 5,597,910 A * | 1/1997 | Gudibande et al. | ...... | 252/301.16 |
| 5,981,286 A * | 11/1999 | Herrmann et al. | ........ | 252/301.16 |
| 6,808,939 B2 * | 10/2004 | Sigal et al. | ..................... | 436/546 |
| 7,108,742 B2 * | 9/2006 | Hall-Goulle et al. | ...... | 106/31.77 |
| 7,416,791 B1 * | 8/2008 | Carlson et al. | ........... | 252/301.16 |
| 7,718,803 B2 * | 5/2010 | Lee et al. | ................... | 106/31.47 |
| 7,750,157 B2 * | 7/2010 | Caputo et al. | ..................... | 546/2 |
| 8,685,276 B2 * | 4/2014 | Aboutanos et al. | ...... | 252/301.26 |
| 8,734,963 B2 * | 5/2014 | De Cola et al. | .......... | 252/301.16 |
| 2006/0022588 A1 * | 2/2006 | Tsuboyama et al. | .......... | 313/504 |
| 2011/0275818 A1 * | 11/2011 | Yersin et al. | ..................... | 546/2 |

FOREIGN PATENT DOCUMENTS

| | | |
|---|---|---|
| EP | 1616929 A2 | 1/2006 |
| WO | 03002974 A2 | 1/2003 |
| WO | 2010037667 A1 | 4/2010 |

OTHER PUBLICATIONS

Iwamura, M., et al.; "Energy-Transfer Process in Crystals of Chiral and Racemic Double Complex Salts of [CO(Ethylenediamine)3] [TB(2, 6-Pyridinedica Rboxylate)3]," Bulletin of the Chemical Society of Japan, Chemical Society of Japan, Jan. 1, 2007, pp. 1140-1147, vol. 80.

Kundu, T., et al.; "Paramagnetic ruthenium-biimidazole derivatives [(acac)2Ru <III>(LHn)] <m>, n/m=2/+, 1/0, 0/−,~. Synthesis, structures, solution properties and anion receptor features in solution state," Dalton Transactions 2010 Royal Society of Chemistry GBR, 2010, pp. 4232-4242, vol. 39, no month available.

Uddin, M. J., et al.; "Emmission Quenching of Double-Complex Salt Crystals of [RUL3]3 [CO[BPYDC)3]2.NH20(L:2,2'-Bipyridin E,2,2'-Bipyrazine or 4,4'-Dimetyl-2,2-Bipyridine, and BPYDC: 2,2'-Bipyridine-4,4'-Dicarbox Ylate)," Bulletin of the Chemical Society of Japan, Chemical Society of Japan, Jan. 1, 1999, pp. 989-996, vol. 72.

International Search Report, May 4, 2012.

* cited by examiner

*Primary Examiner* — Helene Klemanski
(74) *Attorney, Agent, or Firm* — Tristan A. Fuierer; Moore & Van Allen, PLLC

(57) ABSTRACT

The present invention relates to a new family of luminescent pigments consisting of a salt of two ruthenium(II) complex ions of opposite sign charges comprising N-chelating heterocyclic ligands and to their use in security applications to prevent counterfeiting. The invention also refers to ink compositions and to the security documents or secured goods comprising said luminescent pigments.

16 Claims, 3 Drawing Sheets

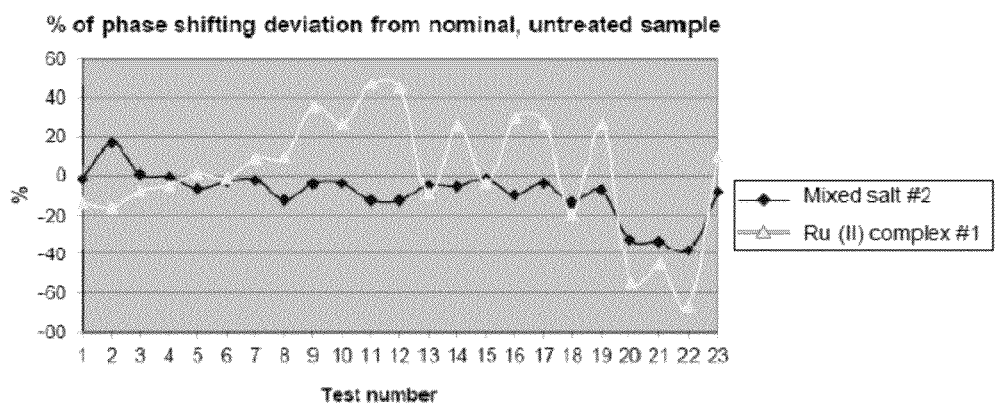

| n° | Test | n° | Test | n° | Test | n° | Test |
|---|---|---|---|---|---|---|---|
| 1 | Ethyl alcohol (95%) | 7 | Sulphuric acid (5%) | 13 | Hydrogen peroxide (5%) | 19 | Durability test with heated air |
| 2 | Acetone (Pure) | 8 | Sodium hypochlorite (5%) | 14 | Diethylene-glycol (Pure) | 20 | Light fastness, blue wool estándar 2 (ISO 105-B01) |
| 3 | Xylene (Pure) | 9 | Sodium hydroxide (5%) | 15 | Tetrachloro-ethylene (Pure) | 21 | Light fastness, blue wool estándar 3 (ISO 105-B01) |
| 4 | Petrol (boiling range 100 – 140°) | 10 | Hot water (60°C) | 16 | Synthetic sweat (DIN 53160) | 22 | Light fastness, blue wool estándar 4 (ISO 105-B01) |
| 5 | Acetic acid (20%) | 11 | Hot water (boiling) | 17 | Abrasion (Vibration test with balls) | 23 | Washing machine test (80 °C) |
| 6 | Hydrochloric acid (5%) | 12 | Washing powder, industrial (95°C) | 18 | Resistance to ironing | | |

Fig. 3

LUMINESCENT PIGMENTS AND THEIR USE IN SECURITY APPLICATIONS

CROSS-REFERENCE TO RELATED APPLICATIONS

This application is filed under the provisions of 35 U.S.C. §371 and claims the priority of International Patent Application No. PCT/EP2012/052307 filed on 10 Feb. 10, 2012 entitled "Luminescent Pigments and Their Use in Security Applications" in the name of Guillermo ORELLANA MORALEDA et al., which claims priority to European Patent Application No. EP 11382034.4, filed on 11 Feb. 2011, both of which are hereby incorporated by reference herein in their entirety.

FIELD OF THE INVENTION

The present invention relates to Ru(II) complex luminescent pigments, to their use in security applications, to ink compositions and to the security documents or secured goods comprising them.

BACKGROUND OF THE INVENTION

Value documents, that are at risk of counterfeiting, are normally provided with various security features to increase their security, so that unauthorized persons cannot undetectably change or reproduce them.

In this regard, the use of luminescent pigments or dyes to detect the validity of documents is generally known within the art. The main type of luminescence used in security documents is photoluminescence, which consists in the emission of light by the luminescent pigment when this is illuminated with light of a different wavelength. Usually the emission of light is produced in the visible range of the electromagnetic spectrum (400 nm-700 nm), when the pigment is excited with ultraviolet radiation (UV). However, other excitation-emission intervals are possible.

Photoluminescence can usually be classified into fluorescence and phosphorescence, depending on the lifetime of the radiation emitted upon excitation with an "instantaneous" pulse of light. "Lifetime" of photoluminescence (or, hereafter, simply "luminescence") can be defined as the inverse of the rate constant of the first order kinetic process through which the spontaneous deactivation of the luminescent electronic state takes place after its formation. When the deactivation occurs through a kinetic process more complex than a first order one, it is usual to estimate a mean photoluminescence lifetime (such as those described by E. R. Carraway, J. N. Demas, B. A. DeGraff and J. R. Bacon, Analytical Chemistry 1991, 63, 337 or E. R. Carraway, J. N. Demas and B. A. DeGraff, Analytical Chemistry 1991, 63, 332). A pigment or dye is said to be "fluorescent" when the emission of light extinguishes after a very short time, on the order of nanoseconds, after excitation of the pigment has stopped. However, a pigment is referred to as "phosphorescent" if the emission of light continues for longer, on the order of milliseconds or more. The term "luminescence" includes all these phenomena, regardless of the duration of the emission.

The use of ruthenium based pigments to secure value documents is known in the art. European patent application EP1616929 discloses luminescent pigments of the family of ruthenium(II) complexes with chelating heterocyclic ligands, for encoding or validating security documents or goods.

Secured articles are commonly exposed to light, changes in temperature, humidity and other environmental perturbations. Consequently, there exists a need for developing security markings with improved stability. Further, security pigments or dyes with more difficult to elucidate structures are also required in order to enhance protection against counterfeiting.

SUMMARY OF THE INVENTION

The invention refers to luminescent pigments consisting of a mixed salt of two opposite sign charged ruthenium(II) complex ions comprising N-chelating heterocyclic ligands, i.e. compounds formed by two ionic Ru(II) complexes that are the counterion of each other. The inventors have surprisingly found that said compounds, compared to the simple Ru(II) complexes with other counterions previously known, show improved resistance to external perturbations.

In addition, compared to Ru(II) complexes comprising chelating heterocyclic ligands whose electric charge is balanced by usual simple counterions such as halides, metal ions, hexafluorophosphate, perchlorate, tetraphenylborate, sulfates, sulfonates, and the like (as those described in EP1616929), the corresponding ruthenium(II) mixed salts afford better results when incorporated to the ink composition via intermediate solvents (such as gamma-butyrolactone, or propylene carbonate) and the resulting ink compositions show enhanced rheological properties.

A further advantage of the pigments of the invention is that their structural elucidation is even more difficult, thus affording greater security against counterfeiting. As these compounds consist of a double ruthenium complex, in order to counterfeit it would be necessary to determine first that it is a complex salt, and not just a simple Ru(II) complex with different ligands, then the structure of the two ruthenium ions and also the ratio of each ion in the mixed salt.

Therefore, in a first aspect the invention is directed to a mixed salt of two opposite sign charged ruthenium(II) complex ions comprising N-chelating heterocyclic ligands. In each Ru(II) complex ion, the ruthenium atom is coordinated to several ligands, which can be identical, similar or different. One of the complex Ru (II) ions has a positive charge, whereas the other one has a negative charge, so that the overall charge of the resulting pigment is neutral.

Said Ru(II) mixed salts show luminescent properties and can thus be used as secured pigments.

According to a second aspect, the invention is directed to an ink composition comprising at least one luminescent pigment of the invention and a vehicle.

A third aspect is a security document or secured good comprising a luminescent pigment or an ink composition of the invention.

A fourth aspect refers to the use of the luminescent pigments or ink compositions of the invention for providing a mark on a document or good for subsequent identification. The pigments or ink compositions of the invention can be incorporated during manufacture of the material used to make the document or good, they can form part of a solid or semi-solid additive that is added to the document or good, or can form part of one or more of the security dyes used in or on the document or good.

The pigments of the invention can be used to make unlimited mixtures and combinations thereof to produce specific luminescence characteristics, and the increased complexity to elucidate their structure makes it even more difficult for a forger to counterfeit security documents or secured goods comprising said pigments.

BRIEF DESCRIPTION OF THE FIGURES

FIGS. 1-3 show the phase-shifting deviation measurement comparison on documents printed with an ink comprising a mixed salt luminescent pigment described in the present invention, versus documents printed with an ink comprising the corresponding precursor pigment based on a ruthenium (II) complex comprising chelating heterocyclic ligands and a simple counterion, as those described in EP1616929, after several chemical and physical resistance tests were performed.

DETAILED DESCRIPTION OF THE INVENTION

Figure 1:
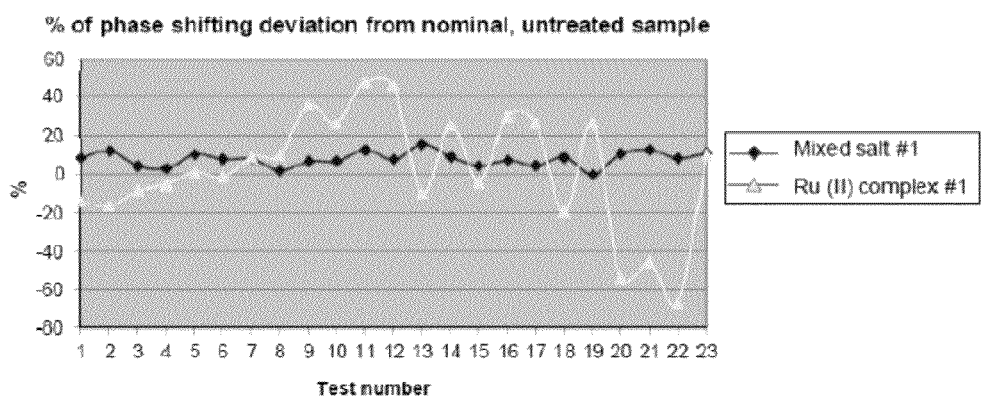

The ligands in the complexes of the present invention represent N-coordinating ligands, i.e. ligands that coordinate to the Ru atom through nitrogen atoms. According to the present invention, the term "N-chelating" or "N-coordinating" refer to ligands or groups that are coordinated to the Ru atom only through N atom(s).

In a particular embodiment of the present invention, at least two ligands in each Ru(II) complex ion are N-chelating heterocyclic ligands.

According to a particular embodiment, the pigment of the invention has formula (I):

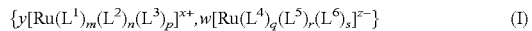

$$\{y[Ru(L^1)_m(L^2)_n(L^3)_p]^{x+}, w[Ru(L^4)_q(L^5)_r(L^6)_s]^{z-}\} \qquad (I)$$

wherein each $L^1$, $L^2$, $L^3$, $L^4$, $L^5$ and $L^6$ is independently selected from N-coordinating monodentate, bidentate or tridentate ligands;

x, y, w and z are independently selected from 1, 2, 3, 4, 5, 6 or a divisor thereof, with the proviso that $x \cdot y = w \cdot z$;

m, n, p, q, r and s are independently selected from 0, 1, 2 or 3, so that each Ru(II) atom is hexacoordinated;

or a solvate thereof.

As mentioned above, N-coordinating ligands $L^1$-$L^6$ are coordinated to the Ru atom only through N atom(s).

The value of x, y, w and z (or a multiple of these figures) is unequivocally determined by the chemical structure and electrical charge of the selected ligands and the 2+ electric charge of the central Ru(II) metal atom. The value of $x \cdot y$ is equal to the value of $w \cdot z$, so that the complex of formula (I) is neutral (i.e. its overall charge is zero).

Preferably, each Ru(II) complex ion contains two or less N-coordinating monodentate ligands, that is, zero, one or two N-coordinating monodentate ligands. Preferably at least two ligands in each Ru(II) complex ion are N-chelating heterocyclic ligands. The value of m+n+p and the value of q+r+s will be 2, 3 or 4, depending on whether ligands $L^1$-$L^6$ represent monodentate, bidentate or tridentate ligands. In one embodiment of the invention, $L^1$-$L^3$ and $L^4$-$L^6$ are selected from N-coordinating bidentate and tridentate ligands. In that case the value of m+n+p will be 2 ($L^1$-$L^3$ tridentated) or 3 ($L^1$-$L^3$ bidentated) and the value of q+r+s will be 2 ($L^4$-$L^6$ tridentated) or 3 ($L^4$-$L^6$ bidentated).

Preferably, $L^1$-$L^6$ are all selected from N-coordinating bidentate ligands. More preferably, $L^1$-$L^6$ are selected from bidentate N-chelating heterocyclic ligands.

N-coordinating monodentate, bidentate and tridentate ligands refer to molecules or ions capable of taking respectively one, two and three coordination sites of the Ru(II) metal core.

In a particular embodiment, N-coordinating monodentate ligands are selected from anionic ligands, such as isothiocyanate (NCS), and neutral ligands. Neutral ligands are preferably selected from heterocyclic molecules, more preferably a 5- to 10-, or a 5- to 6-, membered heterocyclic molecules, such as pyrazole, triazole, tetrazole, pyridine, pyrazine, azepine, benzimidazole, benzothiazole, isothiazole, imidazole, indole, piperidine, piperazine, purine, quinoline, thiadiazole, oxazoline, isoxazoline, thiazoline, and morpholine. In a particular embodiment, N-coordinating monodentate ligands are selected from isothiocyanate and pyridine.

The term "heterocyclic" in the context of the invention refers to a stable 5- to 32-, preferably a 5- to 24- or 5- to 18-, membered heterocyclic group, which consists of carbon atoms and from one to six, preferably 1, 2 or 3, heteroatoms selected from the group consisting of nitrogen, oxygen, and sulphur. The term "5- to 32-membered heterocyclic group" as used herein means a heterocyclic radical having a skeleton of from 5 to 32 atoms. For the purposes of this invention, the heterocycle may be a monocyclic, bicyclic, tricyclic or tetracyclic ring system, which may include bonded or fused ring systems; and the heterocyclyl radical may be partially or fully saturated or aromatic (heteroaryl). Examples of heterocyclic groups include, but are not limited to pyrazole, triazole, tetrazole, pyridine, pyrazine, azepine, benzimidazole, benzothiazole, isothiazole, imidazole, indole, piperidine, piperazine, purine, quinoline, thiadiazole, oxazoline, isoxazoline, thiazoline, morpholine, bipyridine, bipyrazine, terpyridine, phenanthroline, bathophenanthroline, bisoxazoline, bisthiazoline, bisquinoline, bisisoquinoline, quinolinylpyridine, quinolinylphenanthroline and the like. These heterocyclic ligands may be optionally substituted.

The above mentioned groups may be optionally substituted at one or more available positions by one or more suitable groups such as OR', O$^-$, SR', SOR', SO$_2$R', OSO$_2$R', SO$_3$R', SO$_3^-$, NO$_2$, N(R')$_2$, N(R')$_3^+$, N(R')COR', N(R')SO$_2$R', CN, halogen, COR', CO$_2$R', CO$_2^-$, OCOR', OCO$_2$R', OCONHR', OCON(R')$_2$, CONHR', CON(R')$_2$, substituted or unsubstituted $C_1$-$C_{18}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, substituted or unsubstituted $C_1$-$C_{18}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

In another particular embodiment of the invention, N-coordinating bidentate and tridentate ligands are selected from N-chelating heterocyclic ligands.

According to the present invention, a "N-chelating heterocyclic ligand" is a heterocyclic molecule or ion as defined above that is capable of chemical coordination to a metal taking up two (bidentate) or three (tridentate) coordination sites on the Ruthenium(II) metal core by coordination to the metal only through N atom(s). In the case of N-chelating heterocyclic ligands, the heterocyclic group is preferably a 10- to 18-, more preferably a 12- to 18-, membered heterocyclic group. Examples of bidentate or tridentate "N-chelating heterocyclic ligands" include, but are not limited to, ligands comprising a heterocyclic ring selected from pyrazole, triazole, tetrazole, pyridine, pyrazine, azepines, benzimidazole, benzothiazole, isothiazole, imidazole, indole, piperidine, piperazine, purine, quinoline, thiadiazole, oxazoline, isoxazoline, thiazoline, or morpholine; such as bipyridine, bipyrazine, terpyridine, phenanthroline, bathophenanthroline, bisoxazoline, bisthiazoline, bisquinoline, bisisoquinoline, quinolinylpyridines, quinolinylphenanthrolines and the like. These N-chelating heterocyclic ligands may be optionally substituted.

In a particular embodiment, the N-chelating heterocyclic ligand is a polycyclic azaaromatic ligand, namely it is a bicyclic, tricyclic or tetracyclic N-containing aromatic system.

Examples of "polycyclic azaaromatic chelating ligands" include, but are not limited to, bipyridines, bipyrazines, bipyrimidines, terpyridines, phenanthrolines, bathophenanthrolines, bisquinolines, bisisoquinolines, quinolinylpyridines, quinolinylphenanthrolines, pyrazinylthiazoles, pyridylthiazoles, pyrazinylimidazoles, pyridylimidazoles and the like.

According to a preferred embodiment, the N-chelating heterocyclic ligands are selected from optionally substituted 2,2'-bipyridine, 1,10-phenanthroline and bathophenanthroline (4,7-diphenyl-1,10-phenanthroline).

The term "$C_1$-$C_{18}$ alkyl" refers to a linear or branched, cyclic or acyclic, hydrocarbon radical consisting of carbon and hydrogen atoms, containing no insaturation, having between 1 and 18, preferably between 1 and 12, more preferably between 1 and 9, carbon atoms and which is attached to the rest of the molecule by a single bond, including for example and in a non-limiting sense, methyl, ethyl, n-propyl, i-propyl, n-butyl, t-butyl, n-pentyl, etc. Preferably "alkyl" refers to n-nonyl or n-octadecyl.

The terms "alkenyl" and "alkynyl" refer to linear or branched hydrocarbon chain radical having one or more carbon-carbon double bonds or one or more carbon-carbon triple bonds, respectively, and having from two to twelve carbon atoms, and which are attached to the rest of the molecule by a single bond. In an embodiment of the invention the alkenyl or the alkynyl has two to eight, two to six, two or three carbon atoms. The double bond of an alkenyl or the triple bond of an alkynyl group can be unconjugated or conjugated to another unsaturated group. Suitable alkenyl groups include, but are not limited to alkenyl groups such as vinyl, allyl, butenyl, butadienyl, or pentadienyl. Suitable alkynyl groups include, but are not limited to alkynyl groups such as —CCH, —CH$_2$CCH, —CCCH$_3$, —CH$_2$CCCH$_3$.

The term "aryl" refers to an aromatic group having between 6 and 24, preferably between 6 and 18, more preferably between 6 and 16, even more preferably between 6 and 10 carbon atoms, comprising 1, 2, 3 or 4 aromatic rings, bound by means of a carbon-carbon bond or fused, including for example and in a non-limiting sense, phenyl, naphthyl, diphenyl, indenyl, anthryl, phenanthryl, pyrenyl, etc. Preferably "aryl" refers to phenyl.

The term "halogen" refers to bromo, chloro, iodo or fluoro.

According to a particular embodiment, N-chelating heterocyclic ligands are independently selected from ligands comprising a partially saturated or fully unsaturated 10- to 18-, preferably 12- to 14-membered, heterocyclic group that, in addition to the coordinating nitrogen atoms, may optionally contain a further heteroatom selected from N, O and S and may be optionally substituted by one or more substituents selected from OR', O$^-$, SR', SOR', SO$_2$R', OSO$_2$R', SO$_3$R', SO$_3^-$, NO$_2$, N(R')$_2$, N(R')$_3^+$, N(R')COR', N(R')SO$_2$R', CN, halogen, COR', CO$_2$R', CO$_2^-$, OCOR', OCO$_2$R', OCONHR', OCON(R')$_2$, CONHR', CON(R')$_2$, substituted or unsubstituted $C_1$-$C_{18}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, substituted or unsubstituted $C_1$-$C_{18}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

In a preferred embodiment, $L^1$, $L^2$, $L^3$, $L^4$, $L^5$ and $L^6$ are independently selected from isothiocyanate and optionally substituted pyridine, 2,2'-bipyridine, 2,2'-bipyrazine, 2,2',6', 2"-terpyridine, 2,2'-bisquinoline, 2,2'-bisisoquinoline, 1,10-phenanthroline and bathophenanthroline. In a particular embodiment, these groups may be optionally substituted by —SO$_3^-$, CO$_2^-$, NHMe$_2^+$, NO$_2$, methyl, phenyl, nonyl, octadecyloxy, octadecanamide, sulfonatophenyl or carboxylatophenyl.

In a further preferred embodiment, $L^1$, $L^2$, $L^3$, $L^4$, $L^5$ and $L^6$ are independently selected from isothiocyanate, pyridine, 2,2'-bipyridine, 4,4'-dinonyl-2,2'-bipyridine, 4,4'-disulfonato-2,2'-bipyridine, 4,4'-di(sulfonatophenyl)-2,2'-bipyridine, 2,2'-bipyridine-4,4'-dicarboxylate, 2,2'-bipyridine-4,4'-di(4-carboxylatophenyl), 1,10-phenanthroline, N-1,10-phenanthrolin-5-yloctadecanamide, 5-octadecanoxy-1,10-phenanthroline, N,N,N-trimethyl-1,10-phenanthrolin-5-aminium, 4,7-diphenyl-1,10-phenanthroline, 4,7-di(sulfonatophenyl)-1,10-phenanthroline, 4,7-di(4-carboxylatophenyl)-1,10-phenanthroline and 2,6-di(8'-quinolinyl)pyridine.

In a particular embodiment, the opposite sign charged ruthenium(II) complex ions comprising N-chelating heterocyclic ligands of the invention are selected from:

{2[Ru(2,2'-bipyridine)$_3$]$^{2+}$, [Ru(2,2'-bipyridine-4,4'-disulfonate)$_3$]$^{4-}$}, {[Ru(1,10-phenanthroline)$_3$]$^{2+}$, [Ru(2,2'-bipyridine)(2,2'-bipyridine-4,4'-dicarboxylate)$_2$]$^{2-}$}, {2[Ru(4,7-diphenyl-1,10-phenanthroline)$_3$]$^{2+}$, [Ru(2,2'-bipyridine-4,4'-dicarboxylate)$_3$]$^{4-}$}, {2[Ru(2,2'-bipyridine)$_3$]$^{2+}$, [Ru(4,7-di(4-sulfonatophenyl)-1,10-phenanthroline)$_3$]$^{4-}$}, {2[Ru(4,4'-dinonyl-2,2'-bipyridine)$_3$]$^{2+}$, [Ru(4,7-di(sulfonatophenyl)-1,10-phenanthroline)$_3$]$^{4-}$}, {2[Ru(1,10-phenanthroline)$_3$]$^{2+}$, [Ru(4,7-di(sulfonatophenyl)-1,10-phenanthroline)$_3$]$^{4-}$}, or a solvate thereof.

The pigments of the invention may be in the form of solvates. The term "solvate" according to this invention is to be understood as meaning any form of the pigment according to the invention which has one or several other molecule(s) (most likely a polar solvent) attached to it via a non-covalent bonding. Examples of such solvates include hydrates and alcoholates, e.g. methanolates. In a particular embodiment the solvate is a hydrate. The preparation of solvates can be carried out by methods known in the art.

The pigments of the present invention that present a double ruthenium complex ion structure can be prepared by co-precipitation of the two corresponding ruthenium(II) complexes with opposite sign charges. The starting Ru(II) complexes and their process of preparation are known in the art (e.g. EP 1616929, WO 2003/002974). Co-precipitation techniques are also known to those of ordinary skill in the art. In a particular embodiment, the pigments of the present invention are prepared by mixing a solution of a first simple Ru(II) complex with a simple counterion (e.g. halide, hexafluorophosphate, perchlorate or alkanesulfonate) and a solution of a second Ru(II) complex with a simple counterion (e.g. alkaline metal, ammonium or tetraalkylammonium) to form a mixed salt of two opposite sign charged ruthenium(II) complex ions. In a particular embodiment, the co-precipitation process is performed in water; or in a water-soluble solvent, such as methanol or ethanol; or in a halogenated solvent, such as chloroform or methylene chloride; or in mixtures thereof.

The present invention allows for an improved performance of the pigment of the invention when incorporated to security inks. Therefore, a further object of the present invention is an ink composition comprising a pigment according to the present invention and a vehicle.

In this regard, the pigments of the invention have been found to be well soluble only in a small number of solvents, such as propylene carbonate and γ-butyrolactone. Said solvents are compatible with formulations used for printing banknotes (e.g. UV or solvent based screen). The signal produced by the pigments of the invention has shown to be perfectly stable in the inks and also on dried prints.

On the contrary, the inventors found that the precursor Ru(II) complexes with simple counterions, such as those described in EP1616929, are either difficult to incorporate in UV inks as they are soluble in highly polar solvents, which means a strong constraint in terms of formulation and a reduction of the performance of the ink (e.g. in terms of drying), or the incorporation process is rather long. Additionally, in some cases the resulting inks showed a much more pronounced orange colour than those prepared with the double Ru(II) complexes of the invention, which is a clear disadvantage for the formulation of next-to-colorless inks.

Figure 2:
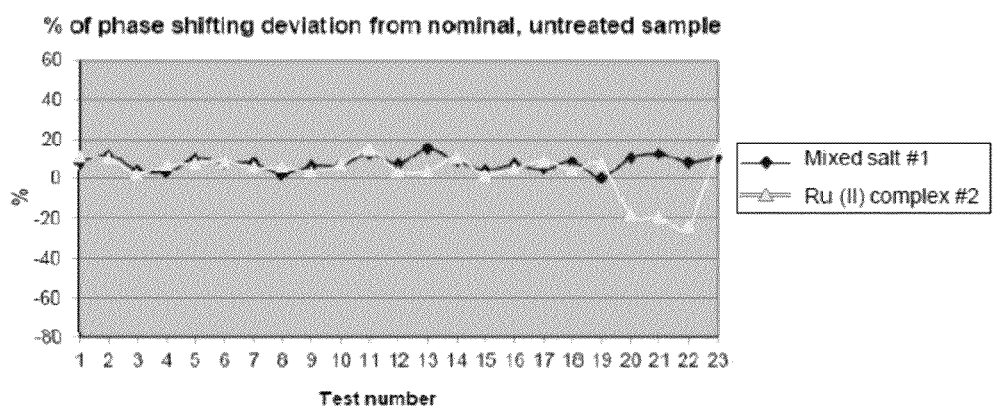

In addition, the chemical and photochemical fastness of the signal resulting from the pigments of the invention on dried prints is highly improved compared to the chemical and photochemical fastness of prints performed with inks based on the simple Ru(II) complexes with chelating ligands and simple counterions. As shown in FIGS. 1-3, phase shifting measurements on documents printed with an ink comprising a complex salt pigment of the invention showed less dispersed values than the corresponding simple ruthenium(II) complexes, as those described in EP1616929, after several artificial ageing tests. These tests included treatment with usual solvents or resistance to water-based solutions (such as laundry, soap, sodium hydroxide, . . . ) even at high temperature.

Tests No. 20, 21 and 22 in FIGS. 1-3 demonstrate that light fastness of the signal on dried prints performed with inks based on the pigments of the present invention can be also improved. Compared to prints performed with inks based on the corresponding simple Ru(II) complexes, the light fastness with the double Ru(II) complexes of the invention is increased by at least a factor of five.

Thus, the pigments of the invention provide improved stability to several chemical or physical external perturbations to which secured articles and goods are usually exposed.

The pigments of the invention can be incorporated into different kinds of inks, including fluorescent, phosphorescent, thermochromic, photochromic or optically variable inks. Preferably, the pigments of the invention are incorporated into optically variable inks, i.e. inks displaying two different colours depending on the angle it is viewed at.

The term "ink composition" or "ink" is well-known in the art and refers to a composition suitable for printing ink on a substrate. Vehicles and/or additives suitable for an ink composition can be determined by those of ordinary skill in view ink type and the printing technique used.

The ink compositions of the invention can be prepared by standard methods known to those of ordinary skilled in the art. In a particular embodiment, the ink composition is prepared by incorporating a pigment of the invention, or a solution thereof, into a previously prepared or known ink composition. In an embodiment, the ink composition is prepared by incorporating a pigment of the invention, or a solution thereof, into an optically variable ink. In a particular embodiment, the pigment of the invention is incorporated into the optically variable ink as a solution in propylene carbonate or in γ-butyrolactone.

In a particular embodiment, the ink composition comprises a pigment of the invention at a concentration of less than 5% of the weight of the ink. Preferably, at a concentration of from about 0.02% to about 5%, more preferably from about 0.05% to 3%, even more preferably from about 0.05% to 1% of the weight of the ink.

The ink composition can comprise two or more pigments of the invention so that it produces specific luminescence characteristics, increasing the security of the document or good.

The ink composition of the invention may be used in offset, intaglio, gravure, lithographic, flexographic, ink jet or silk screen printing processes. Each process has requirements set by the type of printing process employed. Suitable particle size, vehicles, additives and formulation methods for each printing process may be selected by a person skilled in the art.

The term "ink vehicle" is well-known in the art and refers to a vehicle in which the pigment(s) is/are placed to form an ink, i.e. the medium which carries the pigment(s) particles. Any suitable ink vehicle, including aqueous or organic vehicles and combinations thereof, can be used to prepare the ink compositions of the present invention. Examples of suitable organic vehicles include alcohols, aldehydes, ketones, ethers, esters, nitriles and amides. A pure organic solvent or a mixture containing one or more of these solvents can be used as a vehicle. The ink vehicle may comprise water in addition to one or more of the aforesaid organic solvents. Any suitable amount of ink vehicle can be used. Typically the vehicle is in an amount of from about 50% to about 99% by weight, preferably in an amount of from about 80% to about 97% by weight, of the composition.

The ink compositions of the present invention may include further additives, such as resins, electrolytes, pH adjusting agents, humectants, lubricants, solubilizers, surfactants, dispersants, biocides or defoamers.

The ink compositions of the present invention can be prepared by any suitable method known to those skilled in the art. For example, the components can be combined and mixed in a suitable mixer or blender.

In a further aspect, the invention is directed to a security document or secured good comprising a pigment according to the invention.

In the context of the present invention the term "secured good" refers to any article one wants to secure, including identification documents such as identity cards, passports, passes and the like, and valuable documents such as checks, banknotes, bank bills, certificates and the like. According to the present invention, a security document also refers to bulk material or security paper not yet circulatable, precursor to the value document.

In a particular embodiment, the security document or secured good is selected from security paper, an envelope, a check, a banknote, a bank bill, an identity card, a passport, a ticket, a stamp, a pass and a certificate.

The security documents or secured goods may also incorporate two or more pigments according to the invention, instead of only one, in order to produce specific luminescence characteristics, thus increasing the difficulty to counterfeit the document or good. In a particular embodiment, each of said two or more pigments is placed individually in a specific part of the security document or good. In another embodiment, said two or more pigments are incorporated in the same part of the security document or secured good, i.e. in the form of a mixture or combination of pigments.

A further aspect is directed to the use of the pigments or ink compositions of the invention in document security and authentication applications. In an embodiment, they are used to provide a mark on a security document or secured good for subsequent identification. In this way, the pigments or ink compositions of the invention can be used for encoding or validating a security document or secured good.

The pigments or ink compositions can be incorporated in the security document or secured good:
(i) during manufacture of the material used to make the document or good, such as the paper or plastic support used to make said document or good, or
(ii) as part of a solid or semisolid additive added to the document or good, or
(iii) as part of one or more of the security dyes used in or on the article or good.

Another aspect of the present invention refers to a process or method for providing a mark on a security document or secured good comprising applying a pigment or an ink composition according to the present invention onto said security document or secured good. In a particular embodiment, the pigment or ink composition is applied during manufacture of the material used to make the document or good, or as part of a solid or semisolid additive added to the document or good, or as part of one or more of the security dyes used in the article or good.

Another aspect of the present invention is directed to a process or method for identifying security documents or secured goods comprising markings formed using the pigments or ink compositions of the invention. Said process or method comprises subjecting the security documents or secured goods to exciting radiation having a wavelength of from 190 nm to 550 nm; reading said markings by detecting luminescent radiation from said markings; and identifying said security documents or secured goods in response to the reading of said markings.

The present invention will be more precisely explained in the following examples. However, it should be understood that the present invention is not restricted to such examples.

EXAMPLES

Pigments of the present invention consisting of a double ruthenium complex ion structure can be prepared by co-precipitation of the two corresponding ruthenium(II) complexes with opposite sign charges. The starting Ru(II) complexes are known in the art or can be prepared by methods known in the art (e.g. EP 1616929, WO 2003/002974).

General Process of Synthesis of the Pigments of the Invention

The salt pigments of the invention can be prepared by any of the following procedures:

General Procedure A

A first Ru(II) complex comprising chelating heterocyclic ligands is dissolved in methanol and water is added. The resulting precipitate (if any) is removed by filtration followed by washing with water. If no precipitate appears, then water is added to the initial solution.

A second Ru(II) complex comprising chelating heterocyclic ligands is dissolved in water. The resulting solution is dropwise added to the solution of the first Ru(II) complex in water/methanol under stirring. The resulting solution is cooled down and the precipitate formed is filtered out and washed with cold water. The resulting pigment is dried under vacuum or by lyophilization.

General Procedure B

A solution of a first Ru(II) complex comprising chelating heterocyclic ligands in water is dropwise added to the solution of a second Ru(II) complex comprising chelating heterocyclic ligands in methanol. Then, distilled and deionized water is dropwise added under stirring. The resulting mixture is stirred for a few more minutes and the precipitate formed is filtered and washed with cold water. The resulting solid pigment is dried under vacuum.

The following mixed salt pigments can be prepared following any of the above-mentioned procedures.

Example 1

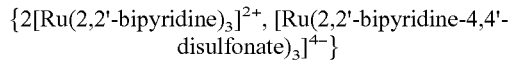
{2[Ru(2,2'-bipyridine)$_3$]$^{2+}$, [Ru(2,2'-bipyridine-4,4'-disulfonate)$_3$]$^{4-}$}

This compound, or a solvate thereof, can be prepared by mixing a solution of [Ru(2,2'-bipyridine)$_3$]Cl$_2$ in methanol or water/methanol and a solution of Na$_4$[Ru(2,2'-bipyridine-4,4'-disulfonate)$_3$] in water, as described in general procedures A and B.

Example 2

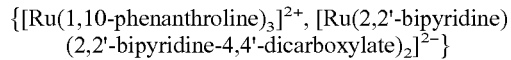
{[Ru(1,10-phenanthroline)$_3$]$^{2+}$, [Ru(2,2'-bipyridine)(2,2'-bipyridine-4,4'-dicarboxylate)$_2$]$^{2-}$}

This compound, or a solvate thereof, can be prepared by mixing a solution of [Ru(1,10-phenanthroline)$_3$]Cl$_2$ in methanol or water/methanol and a solution of the sodium or potassium salt of [Ru(2,2'-bipyridine)(2,2'-bipyridine-4,4'-dicarboxylate)$_2$]$^{2-}$ in water, as described in general procedures A and B.

Example 3

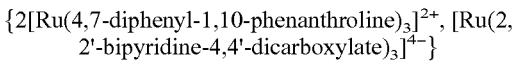
{2[Ru(4,7-diphenyl-1,10-phenanthroline)$_3$]$^{2+}$, [Ru(2,2'-bipyridine-4,4'-dicarboxylate)$_3$]$^{4-}$}

To a solution of [Ru(4,7-diphenyl-1,10-phenanthroline)$_3$]Cl$_2$ (4.437 g) in HPLC grade methanol (300 mL) and purified water (450 mL) was added, under stirring, Na$_4$[Ru(2,2'-bipyridine-4,4'-dicarboxylate)$_3$] (1.638 g). A product precipitated, which was isolated by filtration through a sintered glass plate No. 4 and washed with purified water. The resulting product was dried in a desiccator under vacuum over phosphorous pentoxide for 12 h, yielding the title product (5.360 g, 99.5%).

1H-NMR (300 MHz, DMSO-d$_6$): 8.67 (s, 6H), 8.47 (d, 12H), 8.28 (s, 12H), 7.89 (d, 12H), 7.70-7.49 (m, 66H), 7.50 (d, 6H).

FT-IR (KBr): 2990, 2888, 1614, 1544, 1407, 1364, 770, 703.

Elemental Analysis calculated for C$_{180}$H$_{114}$N$_{18}$.8H$_2$O.3.5CH$_3$COCH$_3$: C, 68.38; H, 4.54; N, 7.51. found: C, 68.40; H, 4.52; N, 7.50.

Spectroscopic and photophysical parameters (propylene carbonate, 25° C.):

| $\lambda^{max}_{abs}$/nm ($\epsilon$/M$^{-1}$ cm$^{-1}$) | $\lambda^{max}_{em}$/nm | $\Phi_{em}^{b}$ | $\tau$/ns ($\alpha_i$/%) | $\tau_{Af}$/ns |
|---|---|---|---|---|
| 280 (302300); 465 (77322) | 620 | 0.18 | 133 (9); 562 (91) | 522 |

Example 4

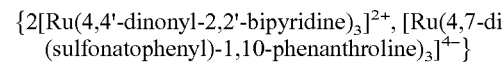
{2[Ru(4,4'-dinonyl-2,2'-bipyridine)$_3$]$^{2+}$, [Ru(4,7-di(sulfonatophenyl)-1,10-phenanthroline)$_3$]$^{4-}$}

To a solution of [Ru(4,4'-dinonyl-2,2'-bipyridine)$_3$]Cl$_2$ (5.026 g) in HPLC grade chloroform (1 L) was added, under stirring, a solution of Na₄[Ru(4,7-disulfonatophenyl-1,10-phenanthroline)₃] (3.336 g) in purified water (250 mL). The two phases were stirred for 2 h and then the aqueous phase was separated. The chloroform phase was washed tih purified water (250 mL) and then concentrated under reduced pressure down to a volume of 500 mL. Then, ethyl acetate (1.5 L) was added and a precipitate was formed, which was isolated by filtration through a sintered glass plate No. 4 and washed with ethyl acetate. The resulting product was dried in a vacuum oven at 50° C. for 12 h, yielding the title product (5.015 g, 66%).

1H-NMR (300 MHz, DMSO-$d_6$): 8.56 (s, 12H), 8.44 (m, 6H), 8.31 (s, 6H), 8.10 (s, 6H), 8.01 (m, 6H), 7.84-7.70 (m, 18H), 7.67 (d, 12), 7.29 (m, 12H), 2.81 (t, 24H), 1.69 (m, 24H), 1.38-1.16 (m, 144H), 0.83 (m, 36H).

FT-IR (KBr): 2924, 2853, 1616, 1469, 1420, 1201, 1121, 1032, 621.

Elemental Analysis calculated for $C_{240}H_{306}N_{18}S_6 \cdot 8.5H_2O$: C, 65.81; H, 7.45; N, 5.76; S, 4.39. found: C, 65.83; H, 7.26; N, 5.78; S, 4.36.

Spectroscopic and photophysical parameters (propylene carbonate, 25° C.):

| $\lambda^{max}_{abs}$/nm ($\epsilon$/M⁻¹ cm⁻¹) | $\lambda^{max}_{em}$/nm | $\Phi_{em}^b$ | $\tau$/ns ($\alpha_i$/%) | $\tau_M$/ns |
|---|---|---|---|---|
| 286 (300500); 463 (66900) | 620 | 0.16 | 272 (58); 655 (42) | 433 |

Example 5

{2[Ru(1,10-phenanthroline)₃]²⁺, [Ru(4,7-di(sulfonatophenyl)-1,10-phenanthroline)₃]⁴⁻}

To a solution of [Ru(1,10-phenanthroline)₃]Cl₂·6H₂O (4.72 g) in a solvent mixture comprising 150 mL of water and 45 mL of ethyleneglycol was added, under stirring, Na₄[Ru(4,7-disulfonatophenyl-1,10-phenanthroline)₃] (5.982 g). A product precipitated, which was isolated by filtration through a sintered glass plate No. 4 and washed with purified water. Then, the product was dissolved in a mixture of methanol:acetonitrile:acetone 7:2:1 (120 mL) and filtered. The filtrate was droopwise added to a diethyl ether (500 mL) under stirring. The resulting precipitates was isolated by filtration through a sintered glass plate No. 4 and washed with a mixture of acetone:diethyl ether 1:1. The resulting product was dried in a vacuum oven at 40° C. for 12 h, yielding the title product (5.175 g, 55.4%).

1H-NMR (300 MHz, DMSO-$d_6$): 8.80 (d, 12H), 8.47-8.38 (m, 18H), 8.11 (m, 6H), 8.10 (d, 12H), 7.94 (m, 12), 7.89-7.59 (m, 30H).

FT-IR (KBr): 3424, 3059, 1626, 1426, 1411, 1194, 1124, 1032, 1009, 846, 723, 618.

Elemental Analysis calculated for $C_{144}H_{90}N_{18}S_6 \cdot 22H_2O \cdot 1CH_3CN$: C, 53.26; H, 4.15; N, 7.99; S, 6.03. found: C, 53.25; H, 3.97; N, 7.96; S, 5.90.

Spectroscopic and photophysical parameters (propylene carbonate, 25° C.):

| $\lambda^{max}_{abs}$/nm ($\epsilon$/M⁻¹ cm⁻¹) | $\lambda^{max}_{em}$/nm | $\Phi_{em}^b$ | $\tau$/ns ($\alpha_i$/%) | $\tau_M$/ns |
|---|---|---|---|---|
| 263 (225000); 448 (64160) | 609 | 0.15 | 213 (51); 648 (49) | 427 |

The invention claimed is:

1. A luminescent pigment consisting of a salt of two Ru(II) complex ions of opposite sign charges comprising chelating heterocyclic ligands and having formula (I):

{$y$[Ru(L¹)$_m$(L²)$_n$(L³)$_p$]$^{x+}$, $w$[Ru(L⁴)$_q$(L⁵)$_r$(L⁶)$_s$]$^{z-}$}   (I)

wherein
each L¹, L², L³, L⁴, L⁵ and L⁶ is independently selected from the group consisting of N-coordinating monodentate, bidentate and tridentate ligands that are coordinated to the Ru atom only through N atom(s);
x, y, w and z are independently 1, 2, 3, 4, 5, 6 or a divisor thereof, with the proviso that x·y =w·z;
m, n, p, q, r and s are independently 0, 1, 2 or 3, so that each Ru(II) atom is hexacoordinated;
or a solvate thereof.

2. A luminescent pigment according to claim 1, wherein N-coordinating bidentate and tridentate ligands are independently selected from the group consisting of polycyclic azaaromatic N-chelating ligands.

3. A luminescent pigment according to claim 1, wherein L¹-L⁶ are independently selected from the group consisting of bidentate and tridentate N-chelating heterocyclic ligands.

4. A luminescent pigment according to claim 1, wherein L¹, L², L³, L⁴, L⁵ and L⁶ are independently selected from the group consisting of optionally substituted pyrazole, triazole, tetrazole, pyridine, pyrazine, azepine, benzimidazole, benzothiazole, isothiazole, imidazole, indole, piperidine, piperazine, purine, quinoline, thiadiazole, oxazoline, isoxazoline, thiazoline, morpholine, bipyridine, bipyrazine, bipyrimidine, terpyridine, phenanthroline, bathophenanthroline, bisquinoline, bisisoquinoline, quinolinylpyridine, quinolinylphenanthroline, pyrazinylthiazole, pyridylthiazole, pyrazinylimidazole and pyridylimidazole.

5. A luminescent pigment according to claim 1, wherein L¹, L², L³, L⁴, L⁵ and L⁶ are independently selected from the group consisting of optionally substituted 2,2'-bipyridine, 2,2'-bipyrazine, 2,2',6',2''-terpyridine, 2,2'-biquinoline, 2,2'-biisoquinoline, 1,10-phenanthroline and bathophenanthroline.

6. A luminescent pigment according to claim 1, wherein L¹, L², L³, L⁴, L⁵ and L⁶ are independently selected from the group consisting of optionally substituted 2,2'-bipyridine, 1,10-phenanthroline and bathophenanthroline.

7. A luminescent pigment according to claim 4, wherein the substituents are selected from the group consisting of —SO₃⁻, CO₂⁻, NHMe₂⁺, NO₂, methyl, phenyl, nonyl, octadecyloxy, octadecanamide, sulfonatophenyl and carboxylatophenyl.

8. A luminescent pigment according to claim 1, wherein L¹, L², L³, L⁴, L⁵ and L⁶ are independently selected from the group consisting of 2,2'-bipyridine, 4,4'-dinonyl-2,2'-bipyridine, 2,2'-bipyridine-4,4'-disulfonate, 4,4'-di(4-sulfonatophenyl)-2,2'-bipyridine, 2,2'-bipyridine-4,4'-dicarboxylate, 2,2'-bipyridine-4,4'-di(4-carboxylatophenyl), 1,10-phenanthroline, N-1,10-phenanthrolin-5-yloctadecanamide, 5-octadecanoxy-1,10-phenanthroline, N,N,N-trimethyl-1,10-phenanthrolin-5-aminium, 4,7-diphenyl-1,10-phenanthroline, 4,7-di(sulfonatophenyl)-1,10-phenanthroline, 4,7-di(4-carboxylatophenyl)-1,10-phenanthroline and 2,6-di(8'-quinolinyl)pyridine.

9. A luminescent pigment according to claim 1, selected from the group consisting of
{2[Ru(2,2'-bipyridine)₃]²⁺, [Ru(2,2'-bipyridine-4,4'-disulfonate)₃]⁴⁻},
{[Ru(1,10-phenanthroline)₃]²⁺, [Ru(2,2'-bipyridine)(2,2'-bipyridine-4,4'-dicarboxylate)₂]²⁻}, {2[Ru(4,7-diphenyl-1,10-phenanthroline)$_3$]$^{2+}$, [Ru(2,2'-bipyridine-4,4'-dicarboxylate)$_3$]$^{4-}$}, {2[Ru(2,2'-bipyridine)$_3$]$^{2+}$, [Ru(4,7-di(4-sulfonatophenyl)-1,10-phenanthroline)$_3$]$^{4-}$}, {2[Ru(4,4'-dinonyl-2,2'-bipyridine)$_3$]$^{2+}$, [Ru(4,7-di(sulfonatophenyl)-1,10-phenanthroline)$_3$]$^{4-}$, {2[Ru(1,10-phenanthroline)$_3$]$^{2+}$,[Ru(4,7-di(sulfonatophenyl)-1,10-phenanthroline)$_3$]$^{4-}$} and a solvate thereof.

10. An ink composition comprising a pigment according to claim 1 and a vehicle.

11. An ink composition according to claim 10, which is for offset, intaglio, gravure, lithographic, flexographic, ink jet or silk screen printing processes.

12. A security document or secured good comprising a pigment according to claim 1.

13. A security document or secured good according to claim 12 which is selected from the group consisting of security paper, an envelope, a check, a banknote, a bank bill, an identity card, a passport, a ticket, a stamp, a pass and a certificate.

14. A method for providing a mark on a security document or secured good for subsequent identification, said method comprising incorporating a pigment according to claim 1 onto the security document or secured good.

15. A method according to claim 14, which comprises incorporating the pigment onto the security document or secured good:

(i) during manufacture of the material utilized to make the document or good, or
  (ii) as part of a solid or semisolid additive added to the document or good, or
  (iii) as part of one or more of the security dyes utilized in or on the article or good.

16. A luminescent pigment according to claim 1, wherein $L^1$-$L^6$ are selected from N-coordinating bidentate ligands.

* * * * *

UNITED STATES PATENT AND TRADEMARK OFFICE
CERTIFICATE OF CORRECTION

PATENT NO.       : 8,986,436 B2                                  Page 1 of 1
APPLICATION NO.  : 13/984710
DATED            : March 24, 2015
INVENTOR(S)      : Orellana Moraleda et al.

It is certified that error appears in the above-identified patent and that said Letters Patent is hereby corrected as shown below:

In the claims

Column 12, Line 28, Claim 4: change "zothiazole, isothiazole, imidazole, indole, pip eridine, pipera-" to -- zothiazole, isothiazole, imidazole, indole, piperidine, pipera- --

Column 14, Line 18, Claim 16: change "$L^1$-$L^6$ are selected from N-coordinating bidentate ligands." to -- $L^1$-$L^6$ are selected from the group consisting of N-coordinating bidentate ligands. --

Signed and Sealed this
Twenty-ninth Day of December, 2015

Michelle K. Lee
*Director of the United States Patent and Trademark Office*